United States Patent
Remcho et al.

(10) Patent No.: US 8,580,161 B2
(45) Date of Patent: Nov. 12, 2013

(54) FLUIDIC DEVICES COMPRISING PHOTOCONTROLLABLE UNITS

(75) Inventors: Vincent Thomas Remcho, Corvallis, OR (US); Jintana Nammoonnoy, Corvallis, OR (US); Myra Koesdjojo, Corvallis, OR (US)

(73) Assignee: State of Oregon acting by and through the State Board of Higher Education on behalf of Oregon State University, Corvallis, OR (US)

( * ) Notice: Subject to any disclaimer, the term of this patent is extended or adjusted under 35 U.S.C. 154(b) by 136 days.

(21) Appl. No.: 13/068,215

(22) Filed: May 4, 2011

(65) Prior Publication Data

US 2011/0272644 A1 Nov. 10, 2011

Related U.S. Application Data

(60) Provisional application No. 61/343,855, filed on May 4, 2010.

(51) Int. Cl.
| | |
|---|---|
| G02B 5/23 | (2006.01) |
| C07D 487/00 | (2006.01) |
| C07D 491/00 | (2006.01) |
| C07D 495/00 | (2006.01) |

(52) U.S. Cl.
USPC ...... 252/586; 204/450; 204/600; 210/321.71; 210/500.29; 210/500.41; 210/645; 548/409

(58) Field of Classification Search
USPC ............... 252/586; 204/450, 600; 210/500.1, 210/500.27, 500.29, 500.41, 644–646, 210/321.71; 548/409
See application file for complete search history.

(56) References Cited

U.S. PATENT DOCUMENTS

| | | |
|---|---|---|
| 3,356,360 A | 12/1967 | Ward |
| 3,695,445 A | 10/1972 | Esmond |

(Continued)

FOREIGN PATENT DOCUMENTS

| | | |
|---|---|---|
| EP | 0 324 922 | 7/1989 |
| GB | 1 289 738 | 9/1972 |

(Continued)

OTHER PUBLICATIONS

Lucia Caprioli, Elisa Mele, Francesco Elio Angilè, Salvatore Girardo, Athanassia Athanassiou, Andrea Camposeo, Roberto Cingolani, and Dario Pisignano, Photocontrolled wettability changes in polymer microchannels doped with photochromic molecules, Applied Physics Letters 91, 113113 2007, © 2007 American Institute of Physics.*

(Continued)

*Primary Examiner* — Bijan Ahvazi
(74) *Attorney, Agent, or Firm* — Klarquist Sparkman, LLP

(57) ABSTRACT

Photochromic materials that are useful for a variety of applications, including for making various unit functions of fluidic devices, particularly microfluidic devices, such as microchannels, valves and gates, using spiropyran materials, such as a polymeric composition comprising a spiropyran. In certain disclosed embodiments the spiropyran is admixed with a polymeric material. For example, the spiropyran may be intercalated into a polyalkylene or polyalkylene phthalate. The spiropyran also may be polymerized with at least one additional monomer to form a heteropolymer, such as by polymerization with styrene, styrene derivatives, acrylate and acrylate derivatives. The spiropyran compositions can be used to make, for example, a photoactuatable valve, a fluidic channel, etc. The valve may be associated with a microchannel, including photochromic microchannel. In certain disclosed embodiments, the valve, at least one microchannel, or both, are re-patternable by light exposure. Embodiments of a method for using a photochromic material in a microfluidic device also are disclosed. One disclosed embodiment concerns providing a microfluidic device comprising at least one re-patternable microchannel defined by a spiropyran photochromic material, at least one photoactuatable valve comprising the same or a different spiropyran photochromic material, or both. Spiropyran photochromic material is serially exposed to light of different wavelengths to move a fluid, to actuate a gate or valve, or both.

14 Claims, 13 Drawing Sheets

(56) References Cited

U.S. PATENT DOCUMENTS

| | | |
|---|---|---|
| 3,762,032 A | 10/1973 | Bowling et al. |
| 3,809,309 A | 5/1974 | Batista |
| 3,827,563 A | 8/1974 | Boe et al. |
| 3,965,008 A | 6/1976 | Dawson |
| 4,080,295 A | 3/1978 | Riede |
| 4,089,456 A | 5/1978 | Toppen et al. |
| 4,100,068 A | 7/1978 | Jordan et al. |
| 4,110,220 A | 8/1978 | Lavender |
| 4,115,273 A | 9/1978 | Winstead |
| 4,155,157 A | 5/1979 | Gersbacher |
| 4,204,628 A | 5/1980 | Houston et al. |
| 4,310,416 A | 1/1982 | Tanaka et al. |
| 4,624,784 A | 11/1986 | Lefebvre |
| 4,647,748 A | 3/1987 | Glassman |
| 4,689,108 A | 8/1987 | Barry, Jr. et al. |
| 4,756,835 A | 7/1988 | Wilson |
| 4,770,787 A | 9/1988 | Heath |
| 4,827,430 A | 5/1989 | Aid |
| 4,869,421 A | 9/1989 | Norris et al. |
| 4,875,619 A | 10/1989 | Anderson et al. |
| 5,087,930 A | 2/1992 | Roy et al. |
| 5,094,749 A | 3/1992 | Seita et al. |
| 5,147,605 A | 9/1992 | Tatsuno et al. |
| 5,232,145 A | 8/1993 | Alley et al. |
| 5,313,023 A | 5/1994 | Johnson |
| 5,316,676 A | 5/1994 | Drori |
| 5,344,392 A | 9/1994 | Senninger et al. |
| 5,385,623 A | 1/1995 | Diaz |
| 5,469,264 A | 11/1995 | Shigemori et al. |
| 5,534,328 A | 7/1996 | Ashmead et al. |
| 5,571,754 A | 11/1996 | Bertin et al. |
| 5,580,523 A | 12/1996 | Bard |
| 5,593,581 A | 1/1997 | Lescoche |
| 5,595,712 A | 1/1997 | Harbster et al. |
| 5,610,645 A | 3/1997 | Moore et al. |
| 5,611,214 A | 3/1997 | Wegeng et al. |
| 5,648,684 A | 7/1997 | Bertin et al. |
| 5,689,966 A | 11/1997 | Zess et al. |
| 5,749,226 A | 5/1998 | Bowman et al. |
| 5,769,985 A | 6/1998 | Kawakami et al. |
| 5,779,833 A | 7/1998 | Cawley et al. |
| 5,811,062 A | 9/1998 | Wegeng et al. |
| 5,813,235 A | 9/1998 | Peterson |
| 5,868,930 A | 2/1999 | Kopf |
| 5,885,456 A | 3/1999 | Charkoudian et al. |
| 5,921,678 A | 7/1999 | Desai et al. |
| 5,932,940 A | 8/1999 | Epstein et al. |
| 5,974,867 A | 11/1999 | Forster et al. |
| 5,985,068 A | 11/1999 | Kawakami et al. |
| 6,024,276 A | 2/2000 | Hirata et al. |
| 6,048,432 A | 4/2000 | Ecer |
| 6,082,891 A | 7/2000 | Schubert et al. |
| 6,100,463 A | 8/2000 | Ladd et al. |
| 6,109,994 A | 8/2000 | Cho et al. |
| 6,121,539 A | 9/2000 | Johnson et al. |
| 6,123,798 A | 9/2000 | Gandhi et al. |
| 6,126,723 A | 10/2000 | Drost et al. |
| 6,129,973 A | 10/2000 | Martin et al. |
| 6,143,247 A | 11/2000 | Sheppard et al. |
| 6,148,635 A | 11/2000 | Beebe et al. |
| 6,167,910 B1 | 1/2001 | Chow |
| 6,192,596 B1 | 2/2001 | Bennett et al. |
| 6,202,312 B1 | 3/2001 | Rando |
| 6,212,333 B1 | 4/2001 | Olk et al. |
| 6,225,497 B1 | 5/2001 | Becker et al. |
| 6,329,139 B1 | 12/2001 | Nova et al. |
| 6,334,301 B1 | 1/2002 | Otsap et al. |
| 6,352,577 B1 | 3/2002 | Martin et al. |
| 6,357,332 B1 | 3/2002 | Vecchio |
| 6,368,505 B1 | 4/2002 | Grummert et al. |
| 6,375,871 B1 | 4/2002 | Bentsen et al. |
| 6,477,058 B1 | 11/2002 | Luebs et al. |
| 6,488,872 B1 | 12/2002 | Beebe et al. |
| 6,490,812 B1 | 12/2002 | Bennett et al. |
| 6,514,412 B1 | 2/2003 | Insley et al. |
| 6,533,840 B2 | 3/2003 | Martin et al. |
| 6,537,506 B1 | 3/2003 | Schwalbe et al. |
| 6,607,644 B1 | 8/2003 | Apffel, Jr. |
| 6,616,877 B2 | 9/2003 | Close et al. |
| 6,616,909 B1 | 9/2003 | Tonkovich et al. |
| 6,623,860 B2 | 9/2003 | Hu et al. |
| 6,635,226 B1 | 10/2003 | Tso et al. |
| 6,652,627 B1 | 11/2003 | Tonkovich et al. |
| 6,654,660 B1 | 11/2003 | Singh et al. |
| 6,656,315 B2 | 12/2003 | Sallavanti et al. |
| 6,666,909 B1 | 12/2003 | TeGrotenhuis et al. |
| 6,672,502 B1 | 1/2004 | Paul et al. |
| 6,676,835 B2 | 1/2004 | O'Connor et al. |
| 6,688,381 B2 | 2/2004 | Pence et al. |
| 6,737,026 B1 | 5/2004 | Bergh et al. |
| 6,744,038 B2 | 6/2004 | Wang et al. |
| 6,749,814 B1 | 6/2004 | Bergh et al. |
| 6,793,831 B1 | 9/2004 | Paul et al. |
| 6,797,056 B2 | 9/2004 | David |
| 6,814,859 B2 | 11/2004 | Koehler et al. |
| 6,838,156 B1 | 1/2005 | Neyer et al. |
| 6,852,231 B2 | 2/2005 | Ivansons et al. |
| 6,863,867 B2 | 3/2005 | Bussche et al. |
| 6,892,781 B2 | 5/2005 | McHerron et al. |
| 6,903,332 B2 | 6/2005 | Weiss et al. |
| 6,911,262 B2 | 6/2005 | Sallavanti et al. |
| 6,913,877 B1 | 7/2005 | Chaplen et al. |
| 6,981,522 B2 | 1/2006 | O'Connor et al. |
| 6,986,428 B2 | 1/2006 | Hester et al. |
| 6,989,134 B2 | 1/2006 | Tonkovich et al. |
| 6,994,829 B2 | 2/2006 | Whyatt et al. |
| 7,014,705 B2 | 3/2006 | David |
| 7,094,345 B2 | 8/2006 | Gilbert et al. |
| 7,097,800 B2 | 8/2006 | Vigna et al. |
| 7,118,920 B2 | 10/2006 | Brophy et al. |
| 7,122,156 B2 | 10/2006 | Bergh et al. |
| 7,125,540 B1 | 10/2006 | Wegeng et al. |
| 7,150,815 B2 | 12/2006 | Ashmead et al. |
| 7,211,442 B2 | 5/2007 | Gilbert et al. |
| 7,264,723 B2 | 9/2007 | Singh et al. |
| 7,279,134 B2 | 10/2007 | Chan et al. |
| 7,378,280 B2 | 5/2008 | Quake et al. |
| 7,501,101 B2 | 3/2009 | Wegeng et al. |
| 7,507,380 B2 | 3/2009 | Chang et al. |
| 7,534,315 B1 | 5/2009 | Singh et al. |
| 2002/0045265 A1 | 4/2002 | Bergh et al. |
| 2002/0108869 A1 | 8/2002 | Savtchenko et al. |
| 2003/0039169 A1 | 2/2003 | Ehrfeld et al. |
| 2003/0052429 A1 | 3/2003 | Vigna et al. |
| 2003/0082066 A1 | 5/2003 | Hajaligol et al. |
| 2003/0156991 A1 | 8/2003 | Halas et al. |
| 2003/0168590 A1 | 9/2003 | Weiss et al. |
| 2003/0183345 A1 | 10/2003 | Soberay |
| 2003/0221777 A1 | 12/2003 | McHerron et al. |
| 2004/0004589 A1 | 1/2004 | Shih |
| 2004/0008370 A1 | 1/2004 | Keane et al. |
| 2004/0012122 A1 | 1/2004 | Nagaoka et al. |
| 2004/0020286 A1 | 2/2004 | Blakley |
| 2004/0022691 A1 | 2/2004 | Allen et al. |
| 2004/0035452 A1 | 2/2004 | Ma |
| 2004/0072278 A1 | 4/2004 | Chou et al. |
| 2004/0084370 A1 | 5/2004 | Singh et al. |
| 2004/0086427 A1 | 5/2004 | Childers et al. |
| 2004/0125689 A1 | 7/2004 | Ehrfeld et al. |
| 2004/0157096 A1 | 8/2004 | Peterson |
| 2004/0208751 A1 | 10/2004 | Lazar et al. |
| 2004/0256230 A1 | 12/2004 | Yager et al. |
| 2005/0007748 A1 | 1/2005 | Callahan et al. |
| 2005/0074834 A1 | 4/2005 | Chaplen et al. |
| 2005/0126211 A1 | 6/2005 | Drost et al. |
| 2005/0129580 A1 | 6/2005 | Swinehart et al. |
| 2005/0145497 A1 | 7/2005 | Gilbert et al. |
| 2005/0179748 A1 | 8/2005 | Malik et al. |
| 2005/0202557 A1 | 9/2005 | Borenstein et al. |
| 2005/0220681 A1 | 10/2005 | Chang et al. |
| 2006/0266692 A1 | 11/2006 | Foster et al. |
| 2007/0020400 A1 | 1/2007 | Chang |
| 2007/0029365 A1 | 2/2007 | Paul et al. |
| 2007/0119771 A1 | 5/2007 | Schukar et al. |

(56) References Cited

U.S. PATENT DOCUMENTS

| | | | |
|---|---|---|---|
| 2007/0125489 | A1 | 6/2007 | Paul et al. |
| 2007/0128707 | A1 | 6/2007 | Rorrer et al. |
| 2007/0131403 | A1 | 6/2007 | Vetrovec et al. |
| 2007/0184576 | A1 | 8/2007 | Chang et al. |
| 2007/0215644 | A1 | 9/2007 | Otis et al. |
| 2007/0278155 | A1 | 12/2007 | Lo et al. |
| 2008/0006040 | A1 | 1/2008 | Peterson et al. |
| 2008/0009780 | A1 | 1/2008 | Leonard et al. |
| 2008/0093298 | A1 | 4/2008 | Browning et al. |
| 2008/0108122 | A1 | 5/2008 | Paul et al. |
| 2009/0165366 | A1 | 7/2009 | Jovanovic et al. |
| 2009/0211977 | A1 | 8/2009 | Miller |
| 2009/0220381 | A1 | 9/2009 | McGimpsey |

FOREIGN PATENT DOCUMENTS

| | | |
|---|---|---|
| WO | WO 2005/045894 | 5/1995 |
| WO | WO 02/40874 | 5/2002 |
| WO | WO 02/076529 | 10/2002 |
| WO | WO 2006/042079 | 4/2006 |

OTHER PUBLICATIONS

Shinji Sugiura, Kimio Sumaru, Katsuhide Ohi, Kazuaki Hiroki,Toshiyuki Takagi, Toshiyuki Kanamori,Photoresponsive polymer gel microvalves controlled by local light irradiation,Sensors and Actuators A 140 (2007) 176-184.® 2007 Elsevier B.V. All rights reserved.*

Masahiro Irie, Akira Menju, and Koichiro Hayashi, Photoresponsive Polymers. Reversible Solution Viscosity Change of Poly(methyl methacrylate) Having Spirobenzopyran Side Groups,vol. 12, No. 6, Nov.-Dec. 1176-1180, 1979.*

Francesca Di Benedetto, Elisa Mele, Andrea Camposeo, Athanassia Athanassiou, Roberto Cingolani, and Dario Pisignano,Photoswitchable Organic Nanofibers, Adv. Mater. 2008, 20, 314-318, ® 2008 Wiley-VCH Verlag GmbH & Co. KGaA, Weinheim.*

De Sousa et al., "Photo-response behavior of electrospun nanofibers based on spiropyran-cyclodextrin modified polymer," *Journal of Materials Chemistry* 20:9910-9917, Sep. 2010.

Delorme et al., "Azobenzene-Containing Monolayer with Photoswitchable Wettability," *Langmuir* 21(26):12278-12282, 2005.

Rosario et al., "Photon-Modulated Wettability Changes on Spiropyran-Coated Surfaces," *Langmuir* 18(21):8062-8069, 2002.

Scarmagnani, "Development of New Adaptive Materials Based on Spiropyran Molecular Photoswitches," Thesis, Dublin City University, 282 pages, Jan. 20, 2010.

Scarmagnani, "Immobilisation and Incorporation of Photochromic Spiropyran Dyes in Polymeric Substrates for Metal Ion Sensing and Micro-Fluidics," *Clarity: Centre for Sensor Web Technologies; Irish Separation Science Cluster;* and *National Centre for Sensor Research,* DCU, Dublin, Ireland, 1 pg., 2008 and 2009.

Sugiura et al., "On-Demand Fluid Control on Microchip by Micro-Patterned Light Irradiation Using Photo-Responsive Hydrogels," *Twelfth International Conference on Miniaturized Systems for Chemistry and Life Sciences,* pp. 838-840, Oct. 12-16, 2008, San Diego, CA.

Sugiura et al., "Photoresponsive polymer gel microvalves controlled by local light irradiation," *Sensors and Actuators A,* 140:176-184, 2007.

Walsh, "Exotic Monoliths," Thesis, Dublin City University, 283 pages, Mar. 30, 2010.

Anastasiadis et al., "Reversibly Photo-Responsive Polymer Surfaces for Controlled Wettability," *Journal of Adhesion Science and Technology* 22:1853-1868, 2008.

Athanassiou et al., "Combination of microstructuring and laser-light irradiation for the reversible wettability of photosensitised polymer surfaces," *Applied Sciences A* 83:351-356, 2006.

Arai et al., "Preparation of photochromic spiropyrans linked to methyl cellulose and photoregulation of their properties," *J. Mater. Chem.* 6(1):11-14, 1996.

* cited by examiner

FLUIDIC DEVICES COMPRISING PHOTOCONTROLLABLE UNITS

CROSS-REFERENCE TO RELATED APPLICATION

This application claims the benefit of the earlier filing date of U.S. Provisional Application No. 61/343,855, filed on May 4, 2010, which is incorporated herein by reference in its entirety.

SUMMARY

The present disclosure concerns photochromic materials that are useful for a variety of applications, including for making various unit functions of devices, particularly microfluidic devices, such as microchannels and valves. These devices may be made using spiropyran materials, including polymeric materials, or a composition comprising a polymeric material, comprising a spiropyran. For certain working embodiments the spiropyran has a formula

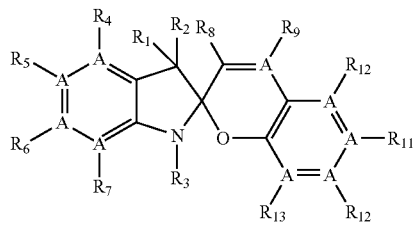

With reference to this general formula, A is independently selected from nitrogen and carbon. $R_1$ and $R_2$ are independently selected from aliphatic and hydrogen. $R_3$ is selected from hydrogen and aliphatic. $R^4$-$R^7$ and $R^{12}$-$R^{13}$ are independently selected from aromatic, aliphatic, alkoxy, cyclic aliphatic, halogen, hydrogen, and functional groups that may be selected to effect the stability of either the ring closed or ring opened compound, including amine, carboxyl, cyano, ester, ether, hydroxyl, nitrogen-bearing functional groups such as nitro, nitroso, sulfate, sulfhydryl and phosphate. $R^8$ and $R^9$ are independently aliphatic, alkoxy or hydrogen. Particular examples of spiropyrans include:

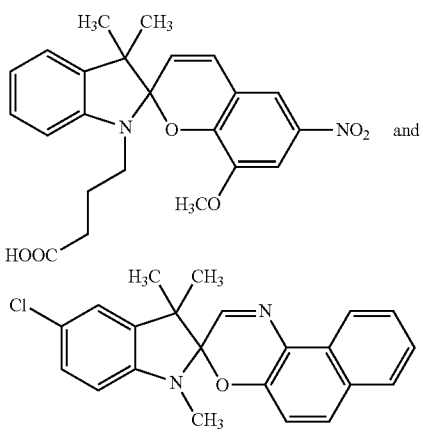

In certain disclosed embodiments the spiropyran is admixed with a polymeric material. For example, the spiropyran may be intercalated into a polyalkylene or polyalkylene phthalate polymer, such as polyethylene phthalate. The spiropyran also may be polymerized with at least one additional monomer to form a heteropolymer. For example, the spiropyran may be polymerized with styrene and styrene derivatives having a formula

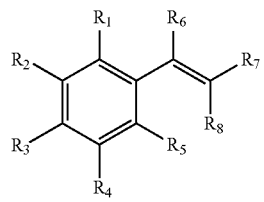

With reference to this general formula, $R^1$-$R^5$ are independently selected from aromatic, aliphatic, alkoxy, cyclic aliphatic, ether, halogen, hydrogen, and functional groups including selected from amine, amide, carboxyl, carboxylic acid, ester, nitro, nitroso, sulfate, sulfhydryl, phosphate, $R^6$-$R^8$ are independently selected from aliphatic, and hydrogen. As yet another example, the spiropyran may be polymerized with acrylate and acrylate derivatives having a formula

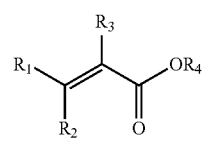

where $R^1$-$R^4$ are independently selected from aliphatic and hydrogen. Examples of such polymeric materials include

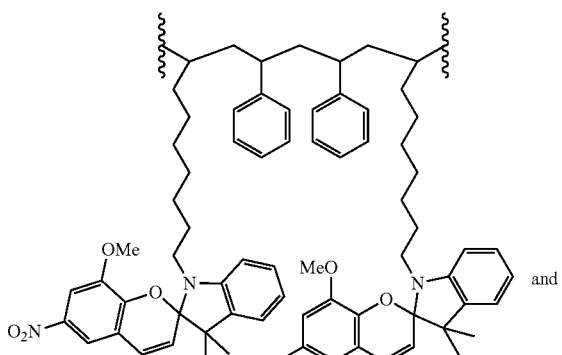

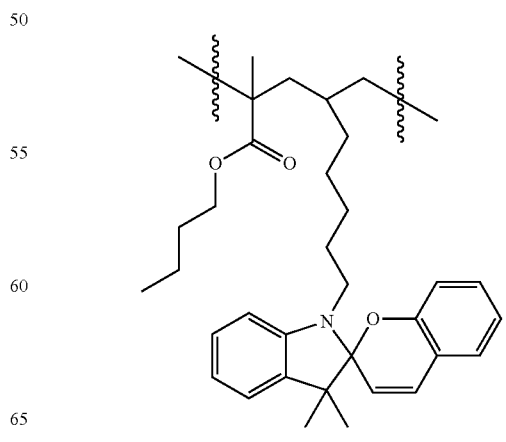

The spiropyran compositions can be used to make, for example, a photoactuatable valve. The valve may be associated with a microchannel, including photochromic microchannel. The photoactuatable valve also may be associated with a microfluidic device. In certain disclosed embodiments, the valve, at least one microchannel, or both, are re-patternable by light exposure. One disclosed embodiment concerns a microwell plate comprising a photoactuatable valve comprising a spiropyran.

Embodiments of a method for using a photochromic material in a microfluidic device also are disclosed. One disclosed embodiment concerns providing a microfluidic device comprising at least one re-patternable microchannel defined by a spiropyran photochromic material, at least one photoactuatable valve comprising the same or a different spiropyran photochromic material, or both. The spiropyran photochromic material is serially exposed to light of different wavelengths to move a fluid, to actuate a gate or valve, or both.

DESCRIPTION OF DISCLOSED EMBODIMENTS

I. Terms and Abbreviations

Figure 1:
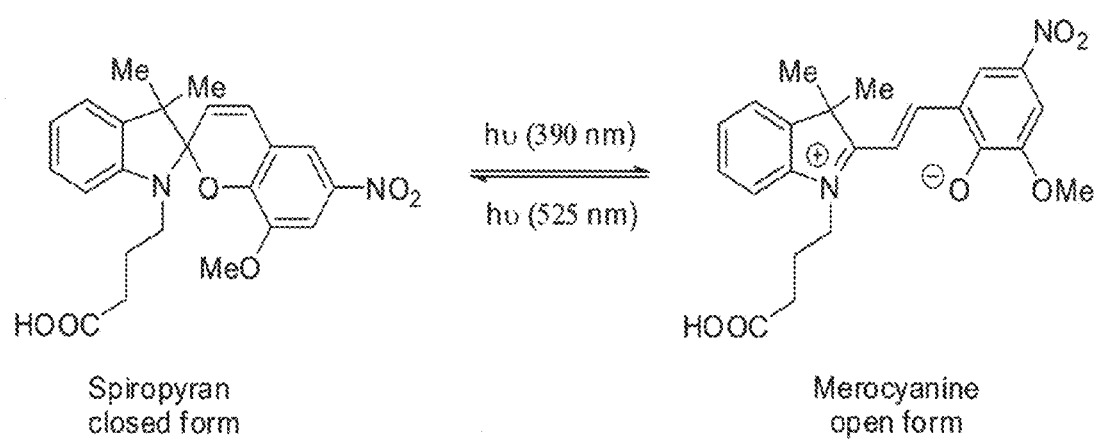
FIG. 1 illustrates the photoisomerization of spiropyran.

Unless otherwise noted, technical terms are used according to conventional usage. As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all molecular weight or molecular mass values, given compounds are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various examples of this disclosure, the following explanations of specific terms are provided:

Aliphatic: A substantially hydrocarbon-based compound, or a radical thereof (e.g., $C_6H_{13}$, for a hexane radical), including alkanes, alkenes, alkynes, including cyclic version thereof, and further including straight- and branched-chain arrangements, and all stereo and position isomers as well.

Amide: An organic functional group characterized by a carbonyl group (C=O) linked to a nitrogen atom and having the following general formula, where R, R' and R" are the same or different, and typically are selected from hydrogen, aliphatic, and aryl.

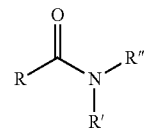

Analog, Derivative: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure.

Aryl: A substantially hydrocarbon-based aromatic compound, or a radical thereof (e.g. $C_6H_5$) as a substituent bonded to another group, particularly other organic groups, having a ring structure as exemplified by benzene, naphthalene, phenanthrene, anthracene, etc.

Arylalkyl: A compound, or a radical thereof ($C_7H_7$ for toluene) as a substituent bonded to another group, particularly other organic groups, containing both aliphatic and aromatic structures.

Carbonyl: Refers to a functional group comprising a carbon-oxygen double bond, where the carbon atom also has two additional bonds to a variety of groups, including hydrogen, aliphatic, such as alkyl, aryl, substituted aryl, heteroaryl, substituted heteroaryl, and the like.

Carboxylic Acid: Refers to a carbonyl-bearing functional group having a formula

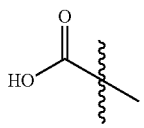

Cyclic: Designates a substantially hydrocarbon, closed-ring compound, or a radical thereof. Cyclic compounds or substituents also can include one or more sites of unsaturation, but does not include aromatic compounds. One example of such a cyclic compound is cyclopentadienone.

Ester: A carbonyl-bearing substituent having a formula

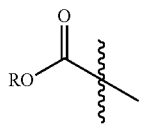

where R is virtually any group, including aliphatic, substituted aliphatic, aryl, arylalkyl, heteroaryl, etc.

Ether: A class of organic compounds containing an ether group, that is an oxygen atom connected to two aliphatic and/or aryl groups, and having a general formula R—O—R', where R and R' may be the same or different.

Functional group: A specific group of atoms within a molecule that is responsible for the characteristic chemical reactions of the molecule. Exemplary functional groups include, without limitation, alkane, alkene, alkyne, arene, halo (fluoro, chloro, bromo, iodo), epoxide, hydroxyl, carbonyl (ketone), aldehyde, carbonate ester, carboxylate, ether, ester, peroxy, hydroperoxy, carboxamide, amine (primary, secondary, tertiary), ammonium, imide, azide, cyanate, isocyanate, thiocyanate, nitrate, nitrite, nitrile, nitroalkane, nitroso, pyridyl, phosphate, sulfonyl, sulfide, thiol (sulfhydryl), disulfide.

Heteroaryl: Refers to an aromatic, closed-ring compound, or radical thereof as a substituent bonded to another group, particularly other organic groups, where at least one atom in the ring structure is other than carbon, and typically is oxygen, sulfur and/or nitrogen.

Heterocyclic: Refers to a closed-ring compound, or radical thereof as a substituent bonded to another group, particularly other organic groups, where at least one atom in the ring structure is other than carbon, and typically is oxygen, sulfur and/or nitrogen.

Ketone: A carbonyl-bearing substituent having a formula

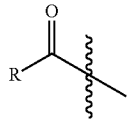

where R is virtually any group, including aliphatic, substituted aliphatic, aryl, arylalkyl, heteroaryl, etc.

Lower: Refers to organic compounds having 10 or fewer carbon atoms in a chain, including all branched and stereochemical variations, particularly including methyl, ethyl, propyl, butyl, pentyl, hexyl, heptyl, octyl, nonyl, and decyl.

Substituted: A fundamental compound, such as an aryl or aliphatic compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a long-chain hydrocarbon may have a substituent bonded thereto, such as one or more halogens, an aryl group, a cyclic group, a heteroaryl group or a heterocyclic group.

Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting. All publications, patent applications, patents, and other references mentioned herein are incorporated by reference in their entirety, unless the context clearly indicates otherwise.

Reactive Groups Any of a variety of groups suitable for coupling a first unit to a second unit as described herein.

II. Introduction

A. Microfluidic Devices

Microfluidic devices have become increasingly popular due to their utility in analysis of minute quantities of samples, their high-throughput sampling capabilities, and their suitability for highly-controlled microreactor embodiments. Versatile and robust microfabrication techniques that allow rapid and cost effective prototyping capabilities are highly desirable in order to make microfluidic devices more available to the research lab and the commercial market.

Digital microfluidics (DMF) is a fluid handling technique that enables manipulation of discrete droplets on an array of electrodes. It utilizes the electrowetting phenomenon to minipulate and move fluid on a two-dimensional electrode array. The working plate is fabricated by patterning arrays of individually controlled electrode plates, where fluid is transported by applying a series of controlled voltage that creates interfacial tension gradients which in turn move the fluid droplet to the charged electrode. Fabrication of a DMF unit cell generally requires electroplating individual electrodes and precise voltage control. The more conventional approach in microfabrication is through a multi step process which usually starts by creating a master template (i.e. by micromachining, electroplating, lithography) that later is used for mass replication. The process is followed by transfer of the master template features to desired substrates (i.e. glass, polymer) through various methods (i.e. etching, embossing, injection molding, casting). The last step in fabrication is the bonding of the microchip to form a complete microchannel. This step can be performed using several different methods, i.e. lamination, gluing, thermal-pressure bonding, laser, and solvent welding. Each steps in the fabrication process can present their own challenges to the realization of the final product. Moreover, in most microfluidic applications, the integration of mechanical pumping and valving mechanisms is often necessary, adding to the complexity of making the device. Each of the additional steps involved in the production process can add up to significantly higher cost, time, and effort.

This technique has been demonstrated for control of small volumes of fluids on a microscale platform, using modest surface forces: the surface area relative to the volume must be small. Limitations in the magnitude of the force achievable B. Photochromophoric/Photoswitchable Materials The disclosed embodiments concern a novel method for making a photochromophore-based devices, such as valves and microfluidic devices. For microfluidic devices, the entire fluidic control scheme, including fluid movement, gating, permeation, valving, etc., may be accomplished via non-mechanical means—powered and manipulated by controlled illumination in desired patterns, intensity and wavelength.

Certain disclosed embodiments concern photo patterned surfaces that afford the possibility of controlling surface wettability, and an approach to utilizing these surfaces in combination with light exposure to achieve microfluidic unit operations. (This is in contrast to manipulation of bulk surface wettability control.) This process mimics the fluid handling mechanism commonly employed in digital microfluidics (DMF) in which a series of electrode plates are utilized to effect control over the transport of fluid droplets by application of a voltage to create an interfacial tension gradient which in turn moves the fluid droplet to the charged electrode. Fluid droplets are moved in like fashion, though not driven by application of voltage to generate the surface tension gradient, but by use of light to alter the structure of a surface immobilized agent (such as a spiropyran) to gate wettability, thus developing a surface tension difference that drives transport. Others have utilized photochromic compounds to control bulk surface wettability. We describe a means of using localized or patterned wettability control to actuate fluid movement across a surface, to function as a valve for fluid transport control (by photo-gating), and to control the passage of fluid through a pore or collection of pores in a microfluidic unit for filtration, osmosis, reverse osmosis, or similar.

Certain disclosed embodiments concern controlling fluid in a traditional microfluidic device, or a microfluidic device made by manipulating an illumination pattern and wavelength on a surface modified with a photochromic compound. The properties of photochromic compounds, such as spiropyran or azobenzene, are used to control the "wettability"— hydrophilicity—of the working surface. This exploits the unique properties of these compounds, such as spiropyran molecules, which upon irradiation with UV or visible light isomerize between a neutral (closed form) and a comparatively more polar zwitterionic (open form) (FIG. 1).

Photochromic compounds are typically deposited on, and potentially covalently immobilized on, the surface of a substrate, and can be used to manipulate the movement of small volumes of fluid in a manner similar to transport of fluids using electric fields in digital microfluidics. In order to better control the wettability of the microfluidic platform, the material of choice and its surface roughness are factors in producing effective surface performance. Photoresponsive wettability of the surface can be enhanced by creating well-ordered structures or pillars using microfabrication and nanofabrication techniques. The microscale or nanoscale features or substrates function as support materials for the photochromic compounds. Various materials including alumina membranes, arrays of Nanosprings®, paper-based filter media and plastics have been made.

Fluid displacement is realized by altering the surface polarity of the photoswitchable materials by irradiation with light at various wavelengths. In certain disclosed embodiments, a coating of photoresponsive molecules covalently bound to a substrate, such as a Nanospring® mat, effectively controlled surface wettability and is useful as a photo-reversible polarity switching platform. This provides novel photoswitchable-based microfluidic devices, where the fluidic unit operations including non-mechanical gating, valving, and pumping, may be enabled using simple light control. Integrating light emitting diode (LED) sources into the system allows production of low cost miniaturized systems.

Fluid movement may be dependent on the relative polarities of the fluid and the surface. It is therefore possible to control the transport of highly polar, semipolar, and nonpolar fluids on various surfaces, suitably prepared. In the instance of a polar fluid (such as an aqueous solution), transport is enabled by illumination of the surface with light to control the local polarity of the surface. Aqueous droplets are transported from a highly non-polar region to a more polar region by successive illumination of the surface (regulated by light control, and switchable to enable transport in any direction). When these steps are repeated, it is possible to manipulate the movement and direction of travel of the fluid droplet on the modified surface in the manner of a pump, though without mechanical means. An additional benefit of the photogated displacement approach is the possibility of reuse of the device by regeneration of the surface after each use and/or re-patterning of features on the original surface, as illustrated below. The device is reusable by repatterning new microchannel features on the same surface.

Using this approach, functional microchannels are realized without the need to create physical structures or channels. All fluid movement is achieved on the coated surface by photogating—light control—hence mechanical components, such as pumps or valves, are realized in functional form and are not a necessity in physical form, as their functions are fully integrated into the device simply through photogating.

Certain disclosed embodiments concern manipulating the hydrophobic/hydrophilic properties of the photochromic compounds (e.g. spiropyran and azobenzene) to form microchannels, without the necessity of creating physical structures/channels. Photo-controllable valves or gates can be incorporated into the chip design using the same basic concept, and hybrid devices (continuing channels and photochromic compound modified surfaces) are also possible. A non mechanical system, having moving parts for pumps or valves, offers significant advantages and simplicity in both design and fabrication. Light-induced polarity changes apply a force on a liquid to actuate it, while valves may be created based on a flow/no-flow mechanism by controlling the passage of fluid. Using light to produce the photochromic-based microfluidic devices provides a means to fulfill the demands of microdevices production and yields devices that are programmable, reconfigurable, and reusable.

III. Spiropyrans

A. Spiropyran Monomers

Spiropyran, spiropyran derivatives, spiropyran polymers, and such compounds deposited on various substrates, such as alumina, silica, cellulosic materials, and nanostructures, such as an array of Nanosprings® (NS), or admixed with materials such as cellulosic media, are used to illustrate the working mechanisms of a photochromic-compound-modulated microfluidic device. The polarity of the immobilized spiropyran can be tuned by exposing it to light of differing wavelength. It is possible to gate surface hydrophobicity in a patterned format through several cycles.

A first general formula for spiropyrans of the present invention is provided below.

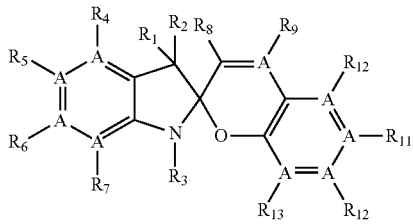

With reference to this first general formula, A is independently selected from nitrogen and carbon, and most typically is carbon. $R_1$ and $R_2$ are selected from aliphatic and hydrogen, more typically alkyl, and even more typically are lower alkyl, such as methyl. $R^3$ typically is a selected from hydrogen and aliphatic, more typically alkyl, alkenyl or alkynyl, or aliphatic groups having functional groups attached thereto, such as acidic functional groups, including acidic functional groups based on carbon, sulfur or phosphorous, with olefins and carboxylic acids being used in particular working examples. $R^4$-$R^7$ and $R^{12}$-$R^{13}$ are independently selected from amine, aromatic, aliphatic, alkoxy, cyclic aliphatic, halogen, hydrogen, and functional groups that may be selected to effect the stability of either the ring closed or ring opened compound, and further maybe selected to facilitate either ring opening or ring closing, and include, without limitation, amine, carboxyl, cyano, ester, ether, hydroxyl, nitrogen-bearing functional groups such as nitro, nitroso, sulfate sulfhydryl, phosphate, etc. $R^4$-$R^7$ and $R^{12}$-$R^{13}$ are most typically hydrogen and/or lower alkyl. $R^8$ and $R^9$ are independently aliphatic, alkoxy or hydrogen, and most typically are hydrogen and/or lower alkyl. Specific examples of spiropyrans include, without limitation:

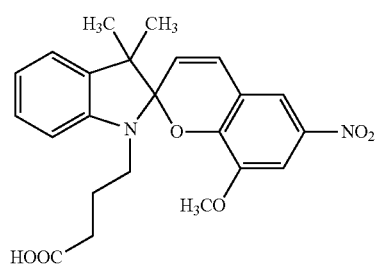

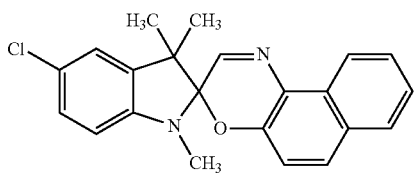

B. Spiropyran Polymers

Certain working embodiments of the present invention have used disclosed spiropyran monomers to form polymeric materials. For example, spiropyrans have been used as monomeric materials to combine with styrene and styrene derivatives

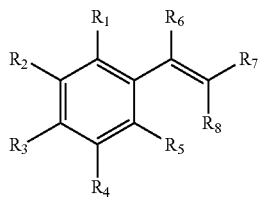

and acrylate and acrylate derivatives

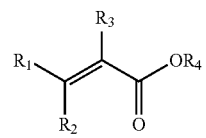

to form heteropolymers comprising such monomeric compounds. With reference to the general formula for styrene, $R^1$-$R^5$ are independently selected from aromatic, aliphatic, alkoxy, cyclic aliphatic, ether, halogen, hydrogen, and functional groups including, without limitation, amine, amide, carboxyl, carboxylic acid, ester, nitro, nitroso, sulfate, sulfhydryl, phosphate, etc. $R^6$-$R^8$ are independently selected from aliphatic, typically alkyl, and hydrogen. With reference to the general formula for acrylate compounds, $R^1$-$R^4$ are independently selected from aliphatic, typically alkyl, and most typically lower alkyl, and hydrogen.

A person of ordinary skill in the art will appreciate that the spiropyran or spiropyran derivative monomer, if it includes a polymerizable moiety such as an olefin, can be the sole monomer used to form a homopolymer comprising just spiropyran or spiropyran derivative monomers. Alternatively, one or more spiropyran or spiropyran derivative monomers can be polymerized with one or more non-spiropyran monomers in substantially equal stoichiometric ratios or unequal stoichiometric ratios to form copolymers. Resulting polymers can have either substantially equal amounts of each monomeric unit, or spiropyran monomers or non-spiropyran monomers can predominate. These spiropyran or spiropyran derivative copolymers can be classified based on how these units are arranged along the chain. Copolymers include, for example, the following arrangements, each of which is within the scope of the present application, where A is a spiropyran or spiropyran derivative, and B is a non-spiropyran: alternating copolymers with regular alternating spiropyran (A) and non-spiropyran (B) units, such as A-B-A-B-A-B; periodic copolymers with A and B units arranged in a repeating sequence, such as A-B-A-A-B-B-A-A-A-B-B-B; statistical copolymers where the sequence of monomer residues follows a statistical rule, such as based on the mole fraction of a monomer residue in the chain, such as A-B-B-B-A-B-A-B-A-A-; block copolymers comprising two or more homopolymer subunits linked by covalent bonds, such as A-A-A-A-B-B-B-B- (block copolymers with two or three distinct blocks are called diblock copolymers and triblock copolymers, respectively); and ter- or higher polymers, which comprise at least three distinct monomers, such as A-B-C-A-B-C-A-B-C.

Schemes 1-3 below illustrate embodiments of a method for making spiropyran-containing polymers, using monomers such as styrenes and acrylates.

Scheme 1

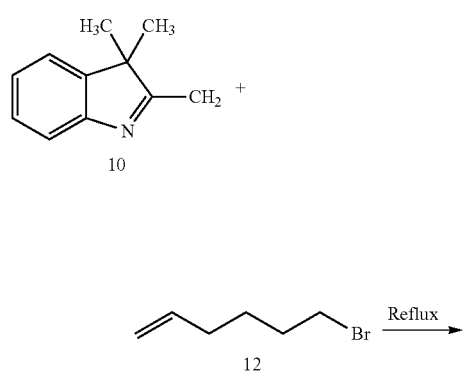

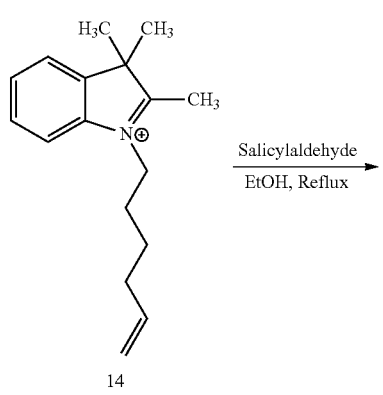

Scheme 2

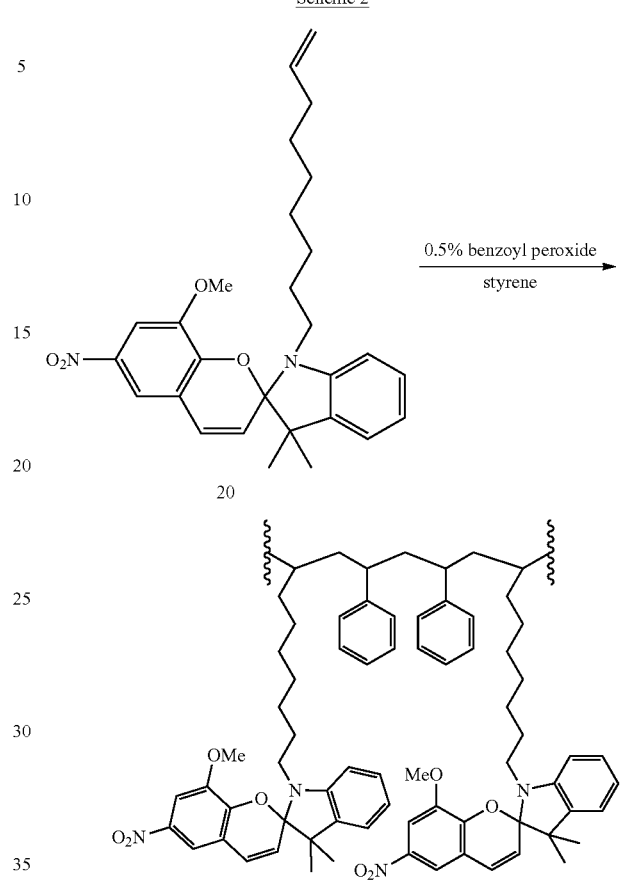

Scheme 3 illustrates the formation of poly(butyl methacrylate)-spiropyran copolymers.

Scheme 3

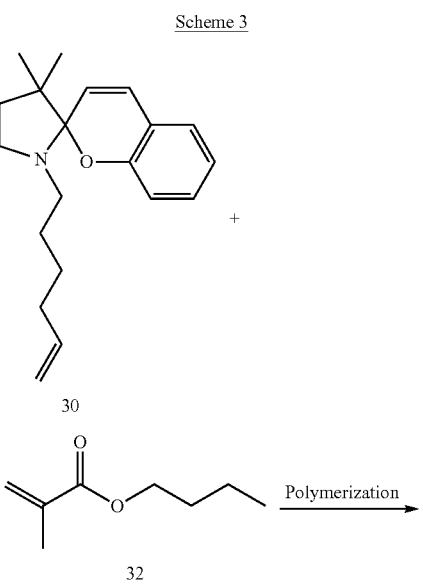

As illustrated in Scheme 1, 2,3,3'-trimethylindoline 10 (Aldrich, St. Louis, Mo., USA) was reacted with 6-bromohexene 12 to alkylate the nitrogen atom of indoline to form compound 14. Compound 14 includes a pendent olefin that is useful for polymerization reactions carried out subsequently. Compound 14 was then refluxed in an alcoholic solution, such as methanol or ethanol, and salicylaldehyde (TCI America, Portland, Oreg., USA) to form spiro compound 16.

Scheme 2 illustrates the polymerization reaction of a spiropyran derivative with styrene monomers to form a spiropyran-styrene heteropolymer. Monomer 20 was combined with styrene and a polymerization catalyst, such as a peroxide, to form the spiropyran-styrene heteropolymer 22. A person of ordinary skill in the art will appreciate that other spiropyran monomers as described above can be used in this process.

-continued

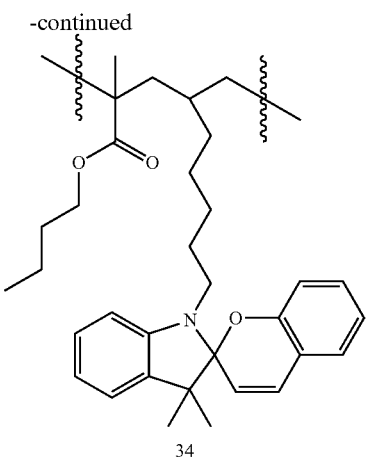

34

As illustrated in Scheme 3, spiropyran derivative 30 was reacted with butyl methacrylate 32 with a polymerization catalyst. This reaction produced poly(butyl methacrylate)-spiropyran copolymers 34.

Figure 2:
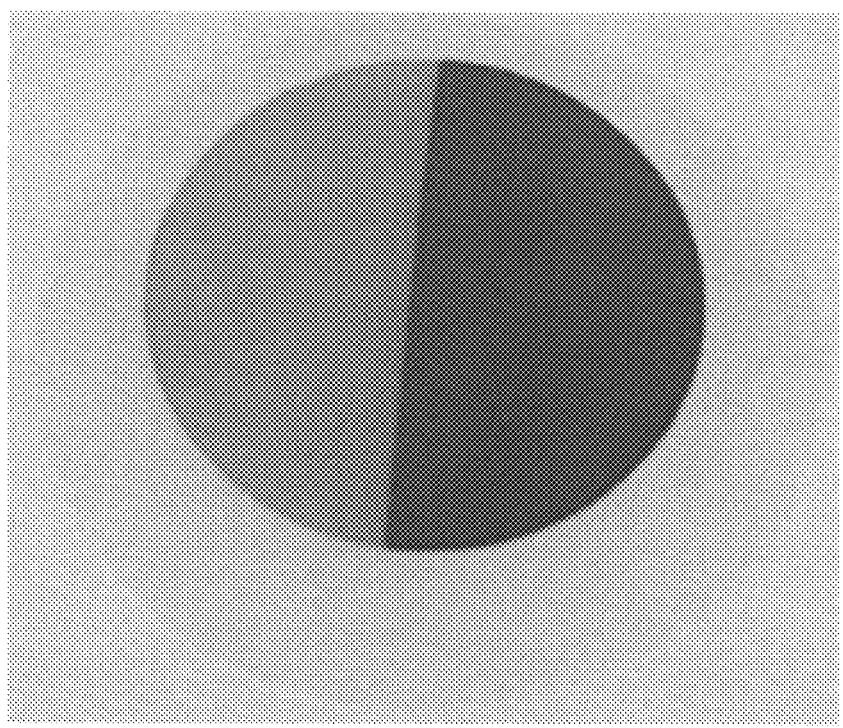
FIG. 2 is a photograph of a spiropyran modified-PET membrane before (colorless—left side) and after (blue—right side) irradiation with UV light.

FIG. 2 is a photograph of a spiropyran modified-PET membrane before (colorless—left side) and after (blue—right side) irradiation with UV light.

IV. Substrates

Photochromic materials, such as embodiments of spiropyrans disclosed herein, can be deposited on a variety of substrates. For example, the materials can be deposited on to metals, metal oxides, semi-metal oxides, ceramics, etc. Particular examples of such materials include silica and alumina. The photochromic materials also can be deposited on polymeric materials, both man made polymers and naturally occurring polymers, such as cellulosic materials, polyalkylene polymers, such as polyethylene and polypropylene, and polyalkylene terephthalate polymers, such as polyethylene terephthalate (PET).

V. Electrospinning

Electrospinning (ES) is a convenient method for synthesizing continuous polymeric fibers with diameters ranging from a few nanometers to several hundred nanometers. This technique is similar to the commercial processes for drawing microscale fibers except for the use of electrostatic repulsion between surface charges (rather than a mechanical or shear force) to continuously reduce the diameter of a viscoelastic jet or a glassy filament. Compared to mechanical drawing, electrospinning is better suited for generating fibers with much thinner diameters, since the elongation can be accomplished via a contactless scheme through the application of an external electric field. Similar to mechanical drawing, electrospinning is also a continuous process and therefore should work well for high-volume production. Electrospun fibers have been employed in many applications of different fields such as tissue engineering, drug delivery, filtration, textiles, sensors, optical and electronic devices, catalysis, etc.

Spiropyran nanofibers offer advantages over other nanomaterials. First, due to their small diameters, they are more sensitive, hence reducing the time necessary for spiropyran nanofiber irradiation. Secondly, instead of immobilizing spiropyran through tedious functionalization processes, spiropyran is incorporated into the fibers during electrospinning, allowing for more spiropyran molecules to be incorporated on the fibers. This in turn leads to a more effective photoisomerization. In addition, the degree of reversibility could also be controlled by selecting the appropriate spiropyran molecule and polymer network. Photochromic fibers could find potential use in areas such as optical sensors, optical gates, and metal filtration.

Spiropyran-based nanofibers produced by electrospinning can be used as photo-controllable gate or valving mechanism in a microfluidic system. The nanofibers were produced by incorporating spiropyran molecules with poly(methyl methacrylate) polymer during electrospinning. With this approach, tedious and complicated immobilization processes are unnecessary. The results are nanofibers that can function as photoactivatable gates allowing for liquid control by light through changes in surface polarity of the fibers.

Figure 3:
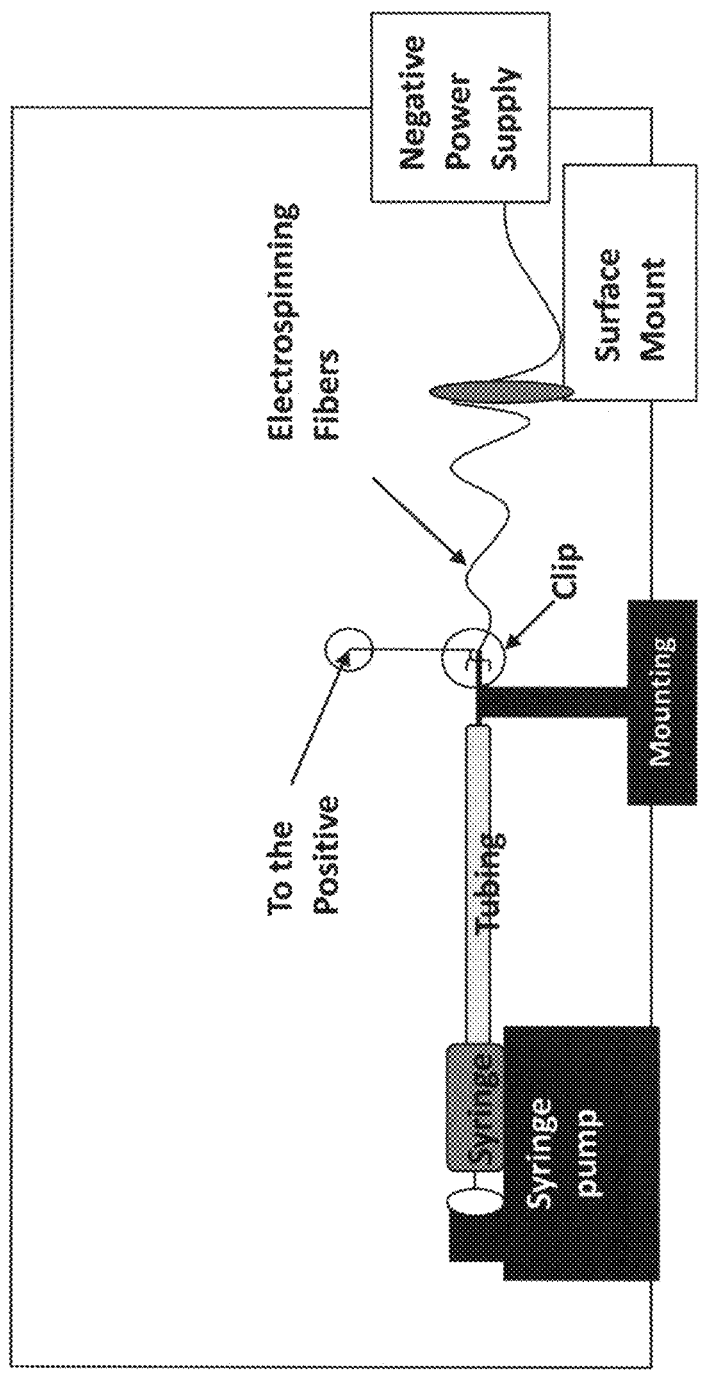
FIG. 3 illustrates one embodiment of an apparatus used to electro spin spiropyran polymeric fibers.
Figure 4:
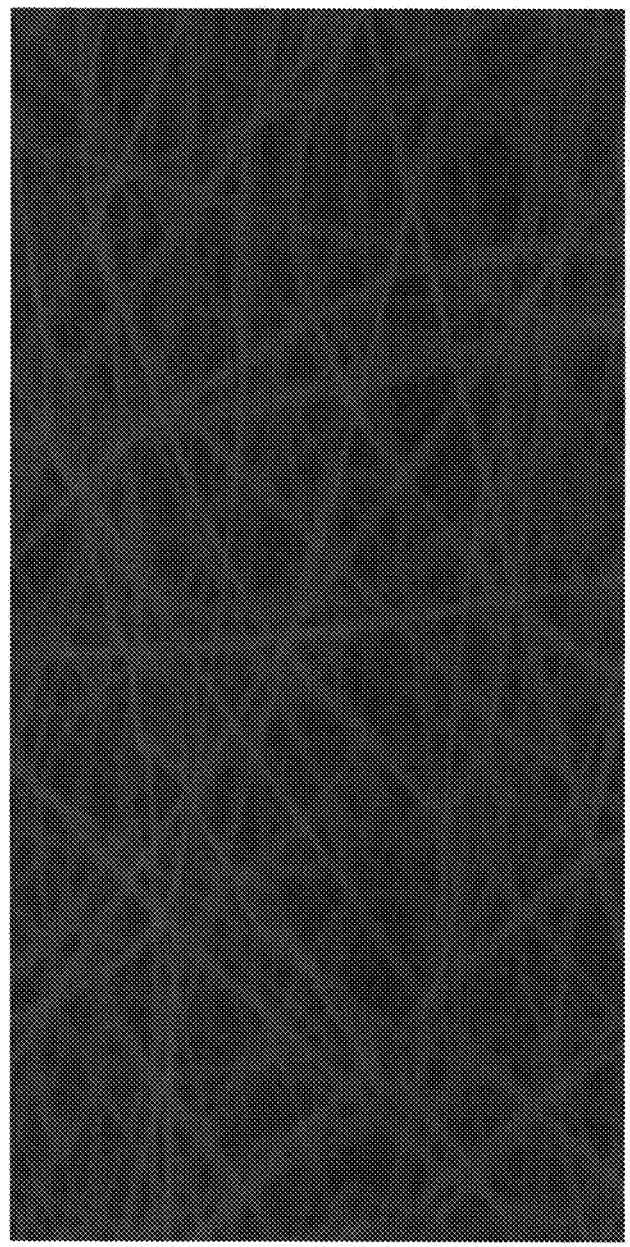
FIG. 4 is an SEM image of spiropyran PMMA nanofibers.

One embodiment of a device used for electrospinning fibers in working embodiments is illustrated in FIG. 3. FIG. 4 is an SEM image of spiropyran-polymethylmethacrylate fibers produced using such an electrospinning device.

Figure 5:
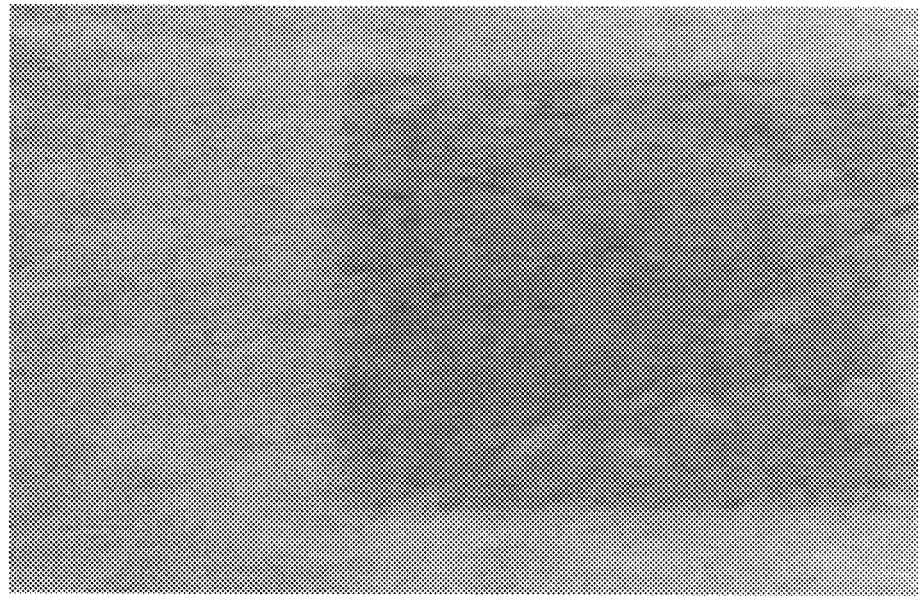
FIG. 5 illustrates spiropyran-PMMA membranes before (colorless) and after (purple) irradiation with UV light (middle).
Figure 6:
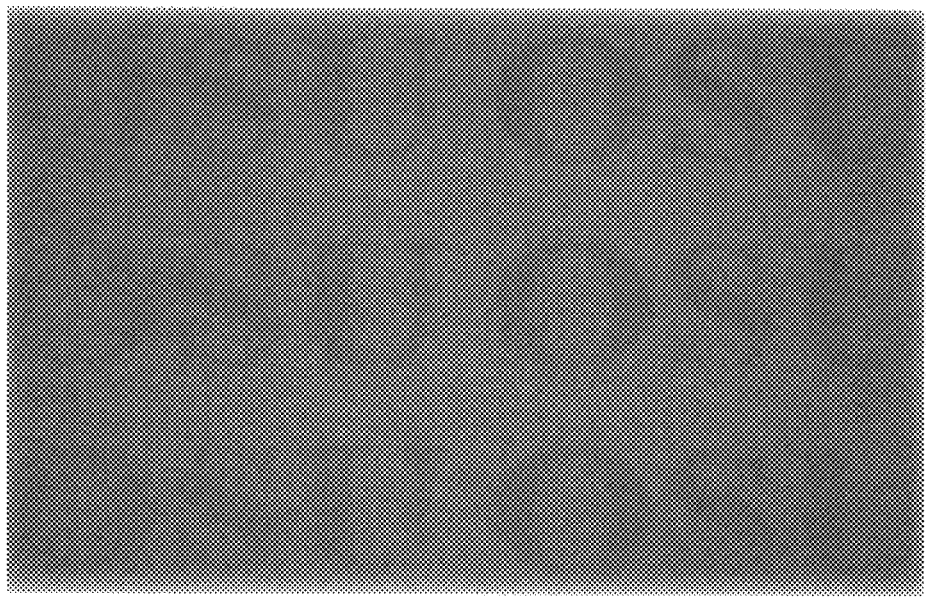
FIG. 6 illustrates nanofibers patterned with UV light.

Spiropyran monomers with various functional groups have been synthesized. These monomers were used as starting material in the electrospinning process to create spiropyran nanofibers. In one disclosed embodiment, (poly)methylmethacrylate (PMMA) was used to prepare a photo-responsive spiropyran nanofiber by electrospinning. The resulting spiropyran-PMMA nanofibers exhibit spiropyran's photoconversion properties after irradiation with UV light (FIGS. 5-6).

VI. Methods for Using Photochromic Materials

A. Fluid Movement Generally

FIG. 1 illustrates the reversible conversion of spiropyran as photochromic dyes that can function as light activated gates or valves. The opening and closing of the valve is controlled solely by irradiation of light of different wavelengths. This process can be utilized to create non-mechanical valving operation in a microfluidic system by simply reversing the polarity of the spiropyran nanofiber. In addition, integration of LED (light emitting diode) sources in the system holds great promise for the production of low cost miniaturized systems.

Figure 7A:
FIGS. 7A and 7B provide water contact angle measurements for an uncoated Nanosprings® mat, contact angle 10°.
Figure 7B:
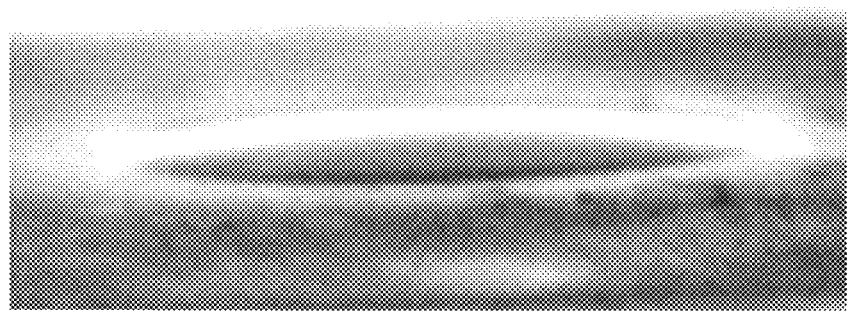
Figure 8A:
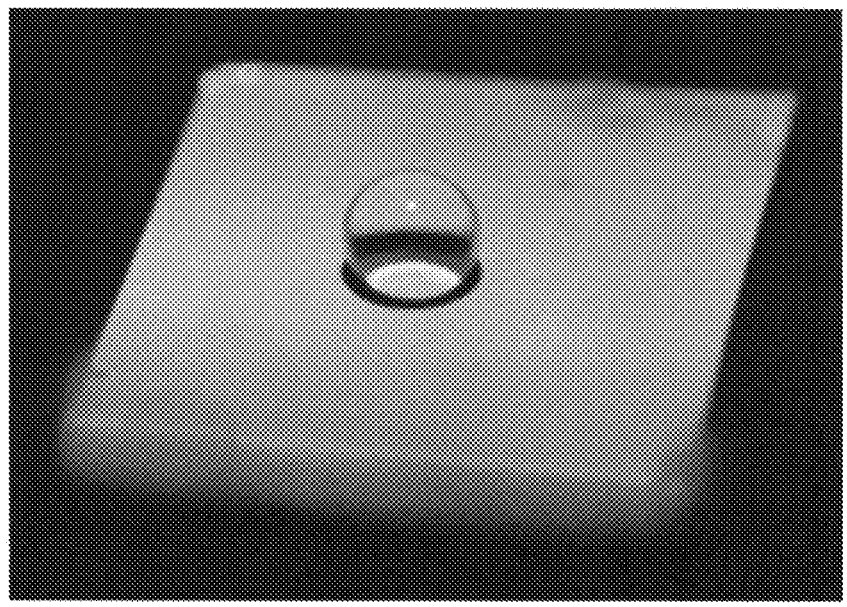
FIGS. 8A and 8B provide water contact angle measurements for spiropyran coated Nanosprings® mat, no light exposure, contact angle 147°.
Figure 8B:
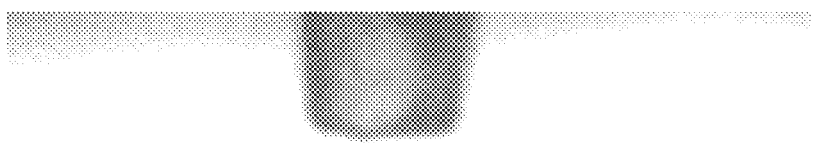
Figure 8B:
Figure 9A:
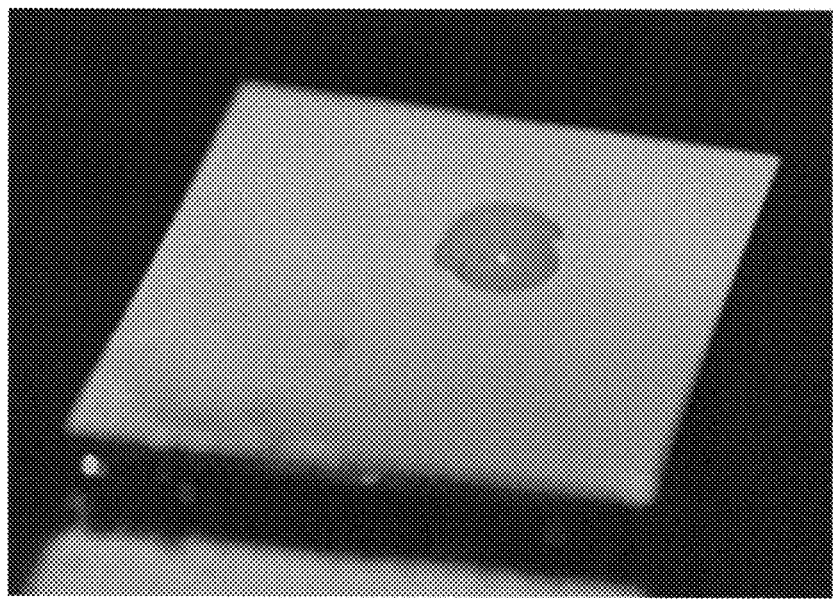
FIGS. 9A and 9B provide water contact angle measurements for spiropyran-coated Nanosprings® mat, after UV irradiation, contact angle 10°.
Figure 9B:
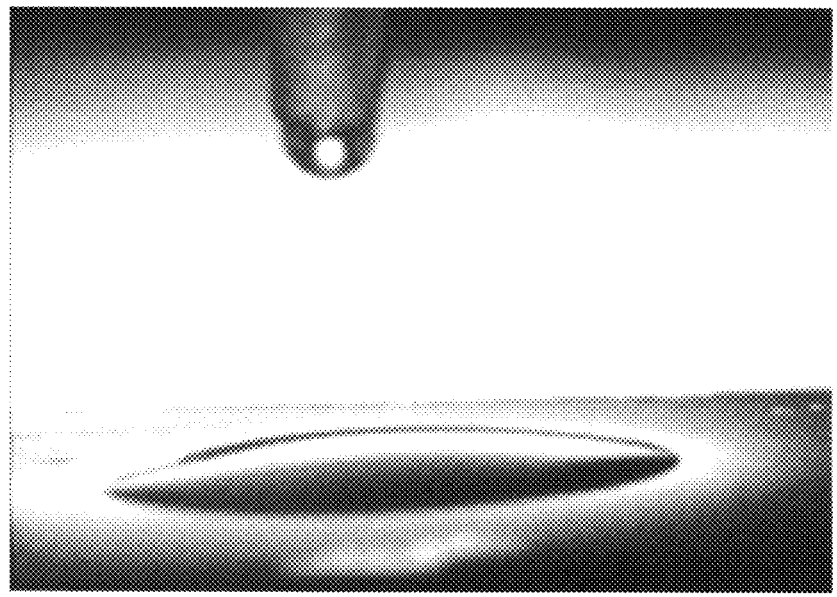

With reference to FIGS. 7-9, an uncoated Nanospring® array is highly hydrophilic. After functionalization with a spiropyran and irradiation with visible light, the Nanospring® array became highly hydrophobic. The surface polarity was reversed on irradiation with UV light, becoming highly hydrophilic. FIGS. 5-7 clearly show these extensive changes in surface polarity.

Figure 10:
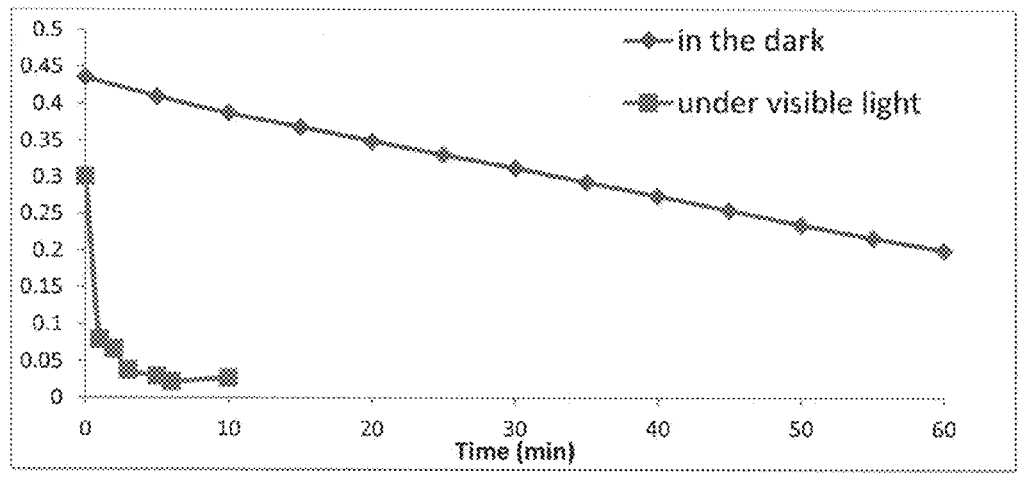
FIG. 10 illustrates decoloration of spiropyran after irradiation with UV light at 535 nanometers.
Figure 11:
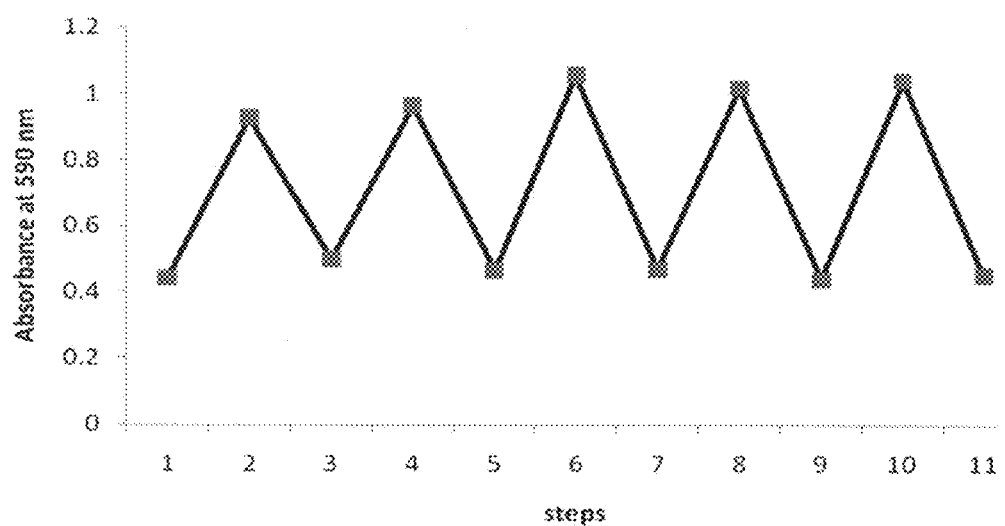
FIG. 11 illustrates photoisomerization of spiropyran-modified polymethyacrylate monitored as a function of absorbance of the closed and open forms at 590 nanometers.

Surface hydrophobicity can be gated in a patterned format through multiple cycles. This is illustrated in FIGS. 10-11.

Figure 12:
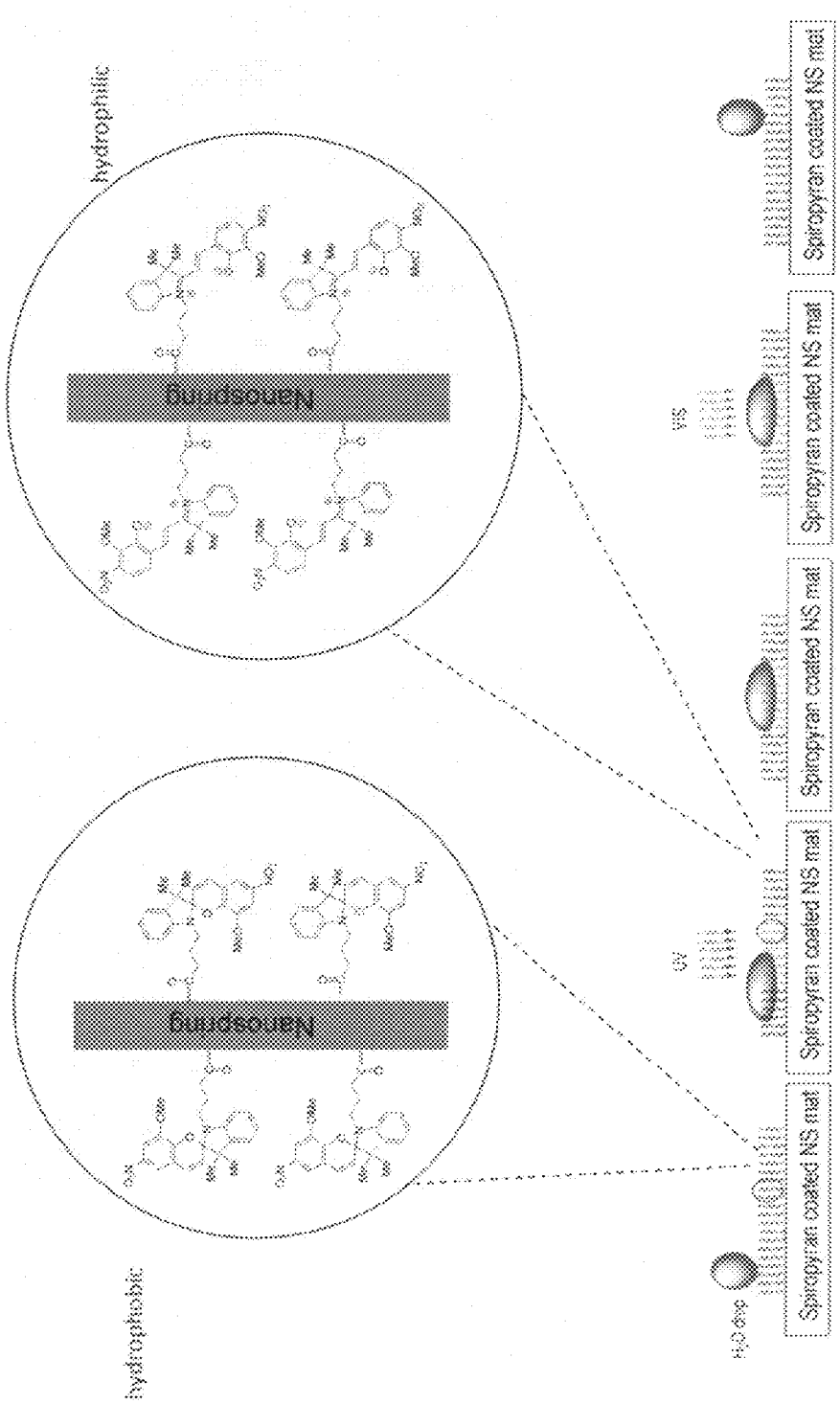
FIG. 12 schematically illustrates fluid movement across a spiropyran coated Nanosprings® mat.
Figure 13:
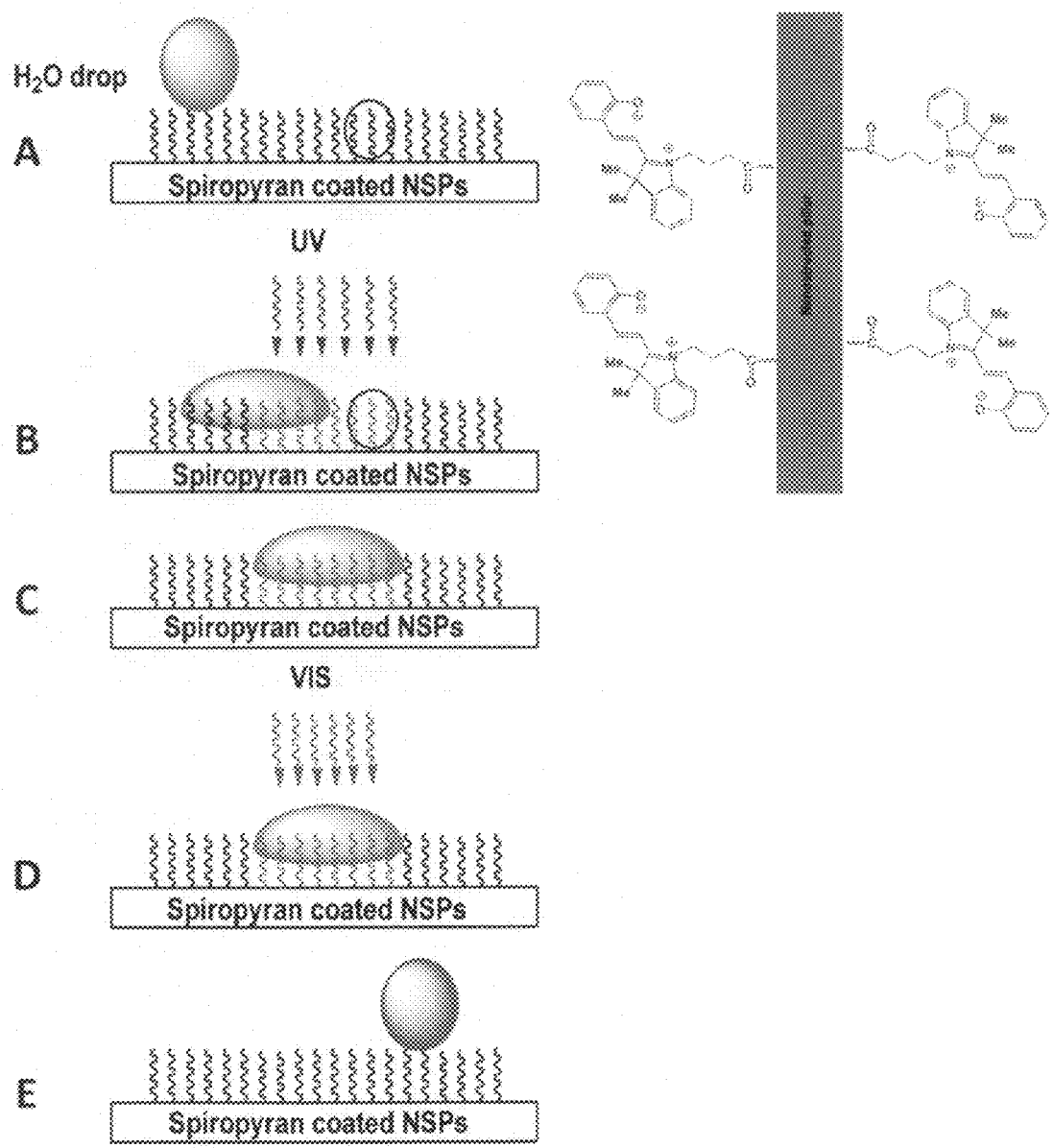
FIG. 13 is a schematic illustration of fluid movement across a spiropyran-coated nanostructured pillar arrays.

FIGS. 12 and 13 illustrate using a photochromic dye to enable a light activated flow scheme, controlled solely by irradiation using different light sources. In FIG. 12, the spiropyran-coated NS (in its closed form) is hydrophobic, illustrated by the water droplet formed on the surface. Next, the area adjacent to the water droplet is exposed to UV light, which renders the surface hydrophilic due to spiropyran ring opening. This in turn causes the water droplet to travel from the highly non-polar to the more polar region of the device as shown in the next frame. Exposure to visible light converts the spiropyran back into its original closed form, regenerating the hydrophobic surface and causing the droplet contact angle to increase. When these steps are repeated, it is possible to manipulate the movement and direction of travel of the fluid droplet on the spiropyran-coated surface by simply controlling the light source and pattern.

FIG. 13 illustrates schematically a high-surface-area, nanostructured planar device useful for droplet microfluidics. The high surface area is necessary to generate (upon irradiation) a considerable change in surface tension sufficient to ensure droplet transport. As shown in FIG. 13, the water droplet on a spiropyran-modified nanostructured pillar (NSP) array moves in the direction of higher surface energy by irradiation with UV light perpendicular to the surface (A to E). With ensuing changes in contact angle (CA), the direction of movement of the droplet is controlled by varying the direction of the travel of the photo-irradiation.

B. Microfluidic Channels

Photochromic materials can be used in combination with traditional microchannels produced, for example, by photolithography. For example, photochromic materials may be deposited in a microchannel, and cycled between two isomeric forms by light to allow fluid to flow, or not, through the microchannel.

Figure 14:
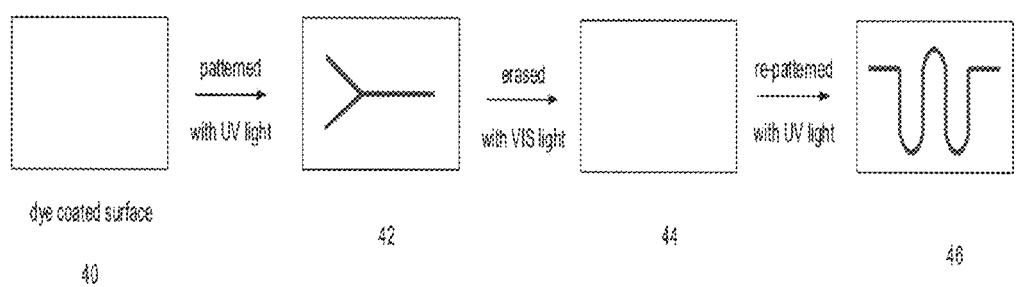
FIG. 14 is a schematic drawing illustrating re-patternable microfluidic channels formed by controlled UV/Vis illumination of a spiropyran-nanofiber surface.

Alternatively, or perhaps in combination, photochromic materials may be used to form microchannels. This process is illustrated schematically in FIG. 14. FIG. 14 illustrates providing a substrate material coated with a photochromic material to form a dye-coated substrate 40. The substrate material can be patterned by applied light of a selected wavelength, such as UV light, to form a desired pattern, such as indicated by patterned substrate 42 of FIG. 14. The patterned areas can be made to have a different hydrophobicity/hydrophilicity relative to other non-patterned areas, such that a fluid can be moved along the substrate, as if the fluid were in a traditional microchannel. The formed pattern also can be erased by applying light to the photochromic material of a different wavelength, such as light in the visible spectrum, to form an erased substrate 44. The substrate can then be re-patterned, either with the same pattern, or a different pattern, and used for the same or different purpose as desired. For example, FIG. 14 illustrates forming an entirely different pattern on the substrate to provide a patterned substrate 46. Using this approach, functional microchannels are realized without the need to create physical structures or channels. All fluid movement is achieved on the modified surface by photogating— light control—hence mechanical components, such as pumps or valves, are realized in functional form and are not a necessity in physical form, as their functions are fully integrated into the device by simply through photogating.

A photo-actuatable paper microfluidic was made by electrospinning spiropyran nanofibers onto a nylon filter paper, as illustrated in FIGS. 5-6. Initially, the coated spiropyran nanofiber paper is highly hydrophobic. A droplet of water placed on the surface forms a bead resulting from the support provided by the highly hydrophobic nanofibers. After of irradiation with UV light, the spiropyran nanofiber surface becomes highly. Post UV exposure, an extensive change was observed in the wettability of the surface where the water droplet immediately permeated into the filter paper.

Figure 15:
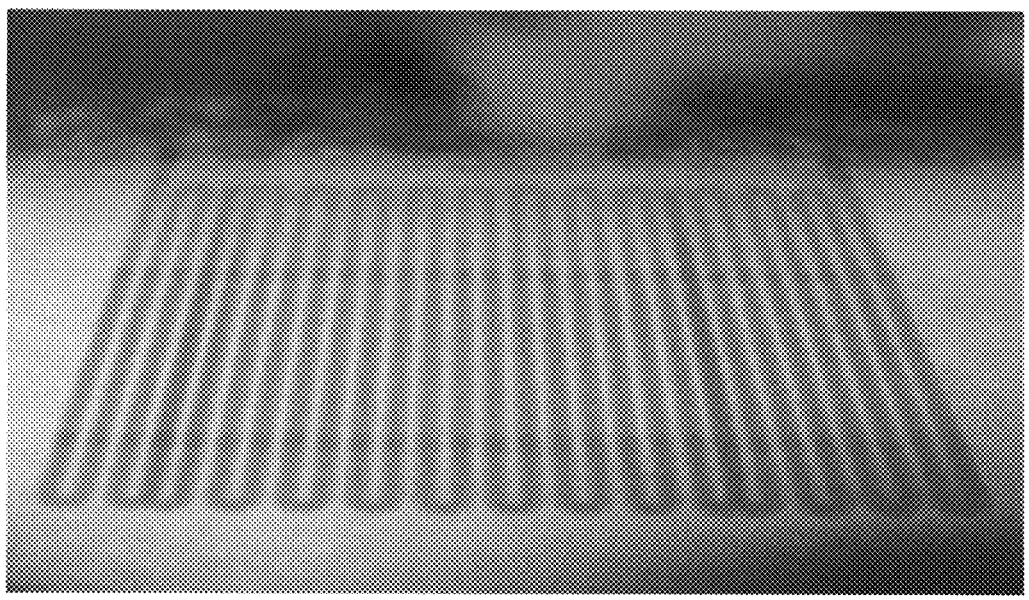
FIG. 15 is a re-patternable microfluidic channel controlled with UV/Vis lights on a spiropyran-nanofiber surface.

FIG. 15 illustrates formation of patterned channels on a spiropyran nanofiber support. The device can be regenerated by re-patterning new features on the same surface.

C. Valves

Figure 16:
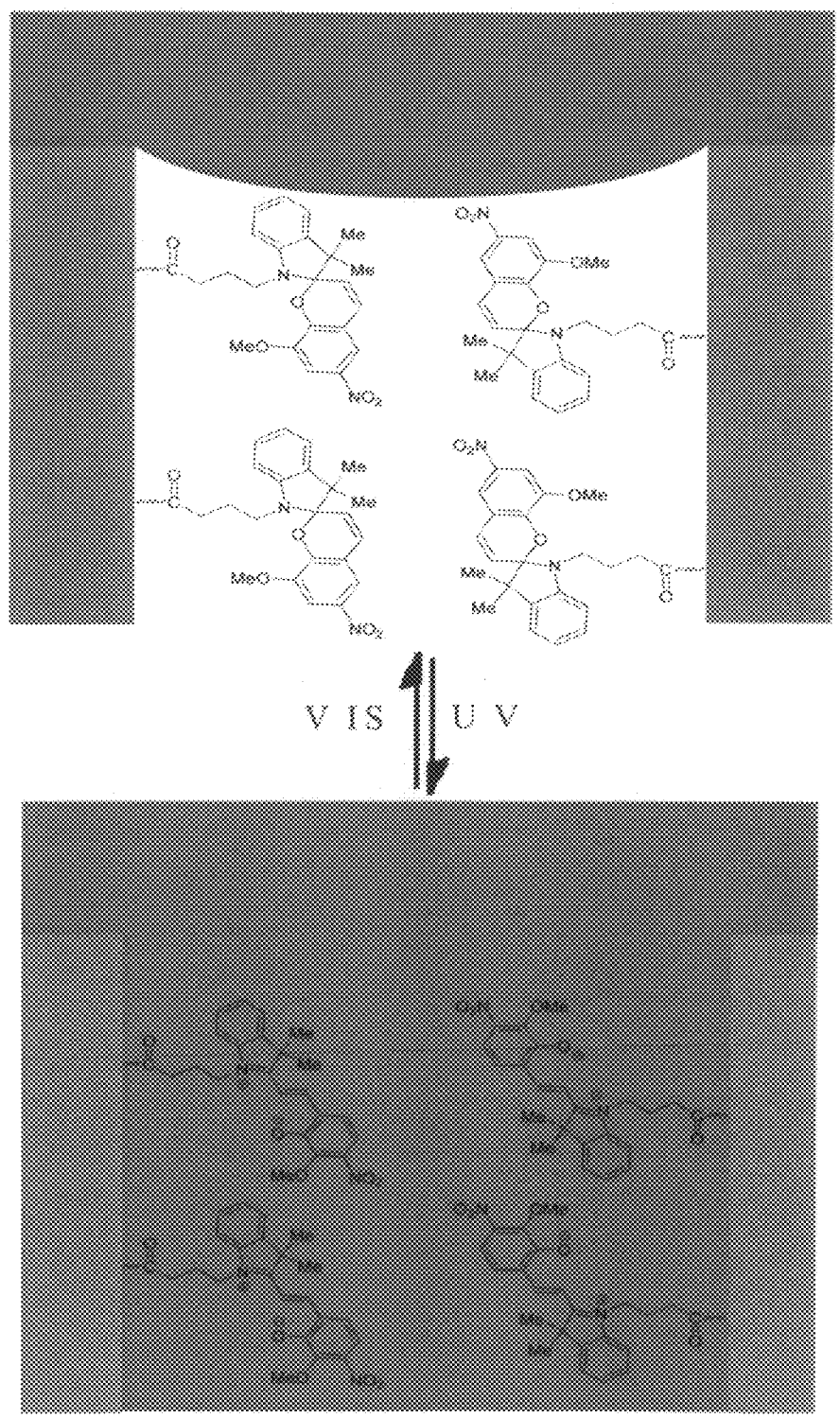
FIG. 16 is a schematic representation of a spiropyran-modified pore surface, illustrating the non-polar closed form before irradiation (preventing flow of an aqueous solution), and the polar open form after irradiation (allowing water to pass through).

Microfluidic devices include various unit operations, such as valves and mixers. Disclosed embodiments of photochromic-based valves, such as spiropyran-based valves, operate by exploiting characteristics where liquid flow is controlled by irradiation with UV/Vis light. FIG. 16 illustrates one embodiment of a disclosed valve. As illustrated in FIG. 16, valves may be created based on a flow/no-flow mechanism by controlling the passage of fluid. With reference to an aqueous or polar fluid, applying UV light to the photochromic material produces a polar, open ring compound that is highly hydrophilic that allows the polar fluid to flow through the illustrated microchannel. Conversely, application of visible light to the photochromic material causes the material to become hydrophobic, thereby precluding polar fluid from flowing through the microchannel.

Figure 17:
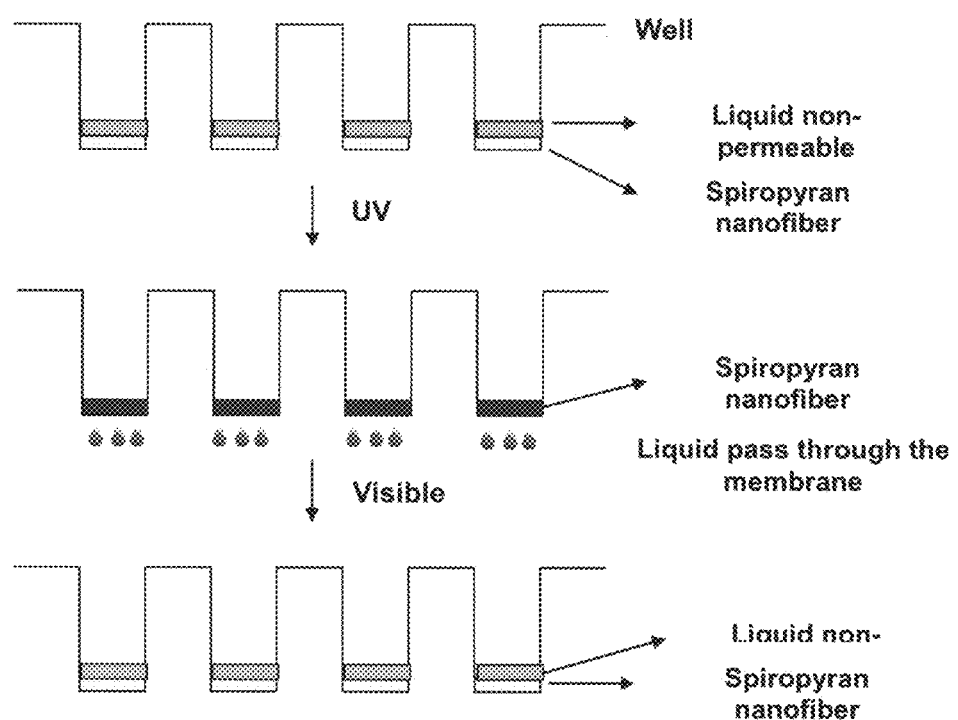
FIG. 17 is a schematic illustration of spiropyran nanofibers used to form a microwell plate having photoactuatable valves.

One example of using photoactivable filter membrane in a microwell plate base is illustrated in FIG. 17. In its closed form, the spiropyran membrane is highly hydrophobic, making it impermeable for any aqueous solution to pass through. Therefore, when the valve is "closed", liquid can be added into the wells and is retained on the surface of the membrane. Upon exposure to UV light, the spiropyran membrane becomes highly hydrophilic and results in the opening of the valve; letting solution to pass through the membrane. The valve can be "re-closed" by exposing it with visible light, converting the membrane to become hydrophobic once again. Well plates equipped with non-mechanical valving base can be tremendously useful in preparative chemistry, where the typical tedious and laborious rinsing is often required.

VII. Working Examples

The following examples are provided to illustrate certain features of working embodiments of the present invention. A person or ordinary skill in the art will appreciate that the scope of the present invention is not limited to the particular features exemplified by these working examples.

Example 1

This Example Concerns a General Synthesis for Preparing Indolenine Salts

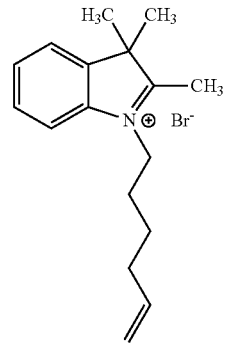 [SMILES: C=CCCCC[N+]1=C(C)C(C)(C)c2ccccc21 ; [Br-]]

A solution of the appropriate 6-bromohexene (1 eq.) in 2,3,3-trimethylindoline (1 eq.) was heated under reflux for 72 hours. After cooling and removal of excess bromoalkene via evaporation under reduced pressure, the resulting viscous purple material was dissolved in chloroform and washed with water (3×). The chloroform layer was dried over anhydrous magnesium sulfate and the solvent removed under reduced pressure. The residue was resuspended in ethanol and shaken with aqueous sodium hydroxide solution. The solution was reduced under vacuum and the product extracted into ether (3×). The ethereal layer was dried over anhydrous magnesium sulfate and the solvent removed under reduced pressure to give the product as a red oil.

Example 2

This example concerns a general synthesis for preparing spiropyran-styrene polymers.

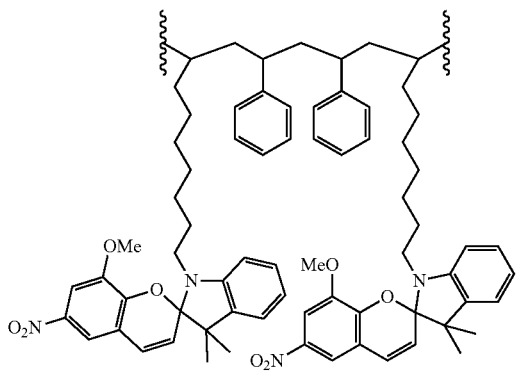 [SMILES: *C(CCCCCCCN1c2ccccc2C(C)(C)C12C=Cc1cc([N+](=O)[O-])cc(OC)c1O2)CC(CC(CC(*)CCCCCCCN1c2ccccc2C(C)(C)C12C=Cc1cc([N+](=O)[O-])cc(OC)c1O2)c1ccccc1)c1ccccc1]

A solution of salicylaldehyde (1 eq.) in methanol was heated to reflux. The indolenine salt (1 eq.), in methanol was added dropwise via a pressure-equalizing dropping funnel over 45 minutes. After the addition, reflux was continued for 20 hours. The reaction mixture was cooled, the resulting yellow precipitate was collected by filtration and washed with cold methanol. The product was purified by column chromatography.

$^1$H-NMR (400 MHz, CDCl$_3$): 1.18 (s, 3H, CH3), 1.32 (s, 3H, CH3), 1.42-1.46 (m, 2H, CH2), 1.62-1.67 (m, 2H, CH2), 2.03-2.08 (m, 2H, CH2), 3.12-3.14 (m, 2H, CH2) 3.24-3.26 (m, 2H, CH2), 4.94-4.97 (d, J=12 MHz, 1H, =CH) alkene, 4.98-5.02 (d, J=16 MHz, 1H, =CH) alkene, 5.69-5.71 (d, J=10 MHz, 1H, =CH) spiro ring, 5.74-5.84 (m, 1H, =CH—) alkene, 6.55-6.57 (d, J=7.6 MHz, 1H, ArH), 6.70-6.72 (d, J=8.4 MHz, 1H, ArH) 6.82-6.85 (d-d, J=9.2 MHz, 2H, ArH), 7.06-7.05 (d, J=7.2 MHz, 1H, ArH), 7.10-7.12 (d, J=8.8 MHz, 1H, ArH), 7.05-7.10 (m, 3H, ArH, =CH), 7.12-7.19 (t, 1H, ArH).

Example 3

This example concerns a general synthesis for preparing poly(butyl methacrylate)-spiropyran copolymers. A solution was made comprising butyl methacrylate and spiropyran in ratio of 4/1 v/v, 0.05 wt % of AIBN in dichloromethane. The mixture was refluxed under nitrogen at 60° C. overnight. The mixture was evaporated under vacuo and precipitated in hexane.

Example 4

This example concerns a general synthesis for electrospinning poly(methyl methacrylate)-spiropyran copolymers. The spiropyran and poly(methyl methacrylate) were dissolved in a mixture of DMF and EtOH (3:2) solution to obtain 20% poly(methyl methacrylate) solution containing spiropyran in 1 wt %. For electrospinning, the apparatus of FIG. 19 was used. The spiropyran and poly(methyl methacrylate) solution was placed in a glass syringe (5 mL) bearing a 27 gauge metal needle which was connected with a high voltage power supply. Target substrate was connected to the copper net collector. Typically, electrospinning was performed at 11 kV voltage, with positive voltage of 8 kV on the needle and negative voltage of 3 kV on the collector. The distance between the needle and the collector was maintained at 18 cm. The flow rate of the solution was controlled by a syringe pump at 0.4 mL/h from the needle outlet. 3 minutes were generally required to obtain sufficiently thick membranes for use in wettability testing.

The present invention has been disclosed with reference to particular preferred or working embodiments. A person of ordinary skill in the art will appreciate that the scope of the invention is not limited to the particular embodiments disclosed to exemplify the invention.

We claim:

1. A photoactuatable valve comprising a polymer comprising a spiropyran monomer, wherein the spiropyran monomer is in a hydrophilic, open-ring conformation when illuminated by ultraviolet light thereby opening the valve to polar fluid, wherein the spiropyran monomer is in a hydrophobic, closed-ring conformation when illuminated by visible light thereby closing the valve to the polar fluid, and wherein the polymer has a formula

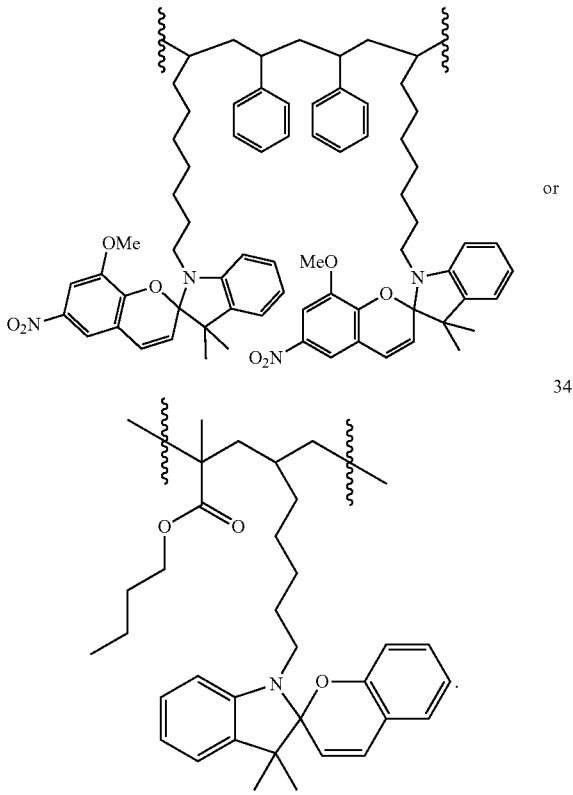

2. The valve according to claim 1 associated with a fluid flow path.

3. The valve according to claim 2, wherein the fluid flow path is a photochromic fluid flow path.

4. The valve according to claim 3, wherein the photoactuatable valve is associated with a microfluidic device.

5. The valve according to claim 4, wherein the valve, at least one fluid flow path, or both, are re-patternable by light exposure.

6. The valve according to claim 2, wherein the associated fluid flow path is a photo-defined fluid flow path formed by applying UV light in a desired pattern to a substrate comprising a polymer comprising a spiropyran monomer.

7. The valve according to claim 6, wherein the associated fluid flow path is linear and defines a functional microchannel on the substrate surface.

8. A microwell plate comprising the photoactuatable valve according to claim 1, comprising a polymer membrane, wherein the polymer comprises a spiropyran monomer, and wherein the photoactuatable valve is impermeable to an aqueous solution when exposed to visible light and permeable to the aqueous solution when exposed to UV light.

9. The microwell plate according to claim 8, wherein the polymer membrane is formed from a plurality of fibers comprising the polymer.

10. A method for using a photochromic material in a microfluidic device, comprising:
    providing a microfluidic device comprising at least one re-patternable fluid flow path defined by a spiropyran photochromic material, at least one photoactuatable valve according to claim 1, comprising the same or a different spiropyran photochromic material, or both; and
    serially exposing spiropyran photochromic material to light of different wavelengths to move a fluid, to actuate a gate or valve, or both.

11. The photoactuatable valve according to claim 1, wherein the polymer comprises the spiropyran monomer polymerized with at least one additional monomer, either in equal stoichiometric ratios or unequal stoichiometric ratios, to form a heteropolymer.

12. The photoactuatable valve according to claim 11, wherein the at least one additional monomer is styrene, acrylate, a styrene derivative having a formula

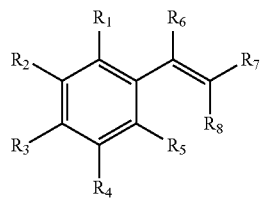

where $R_1$-$R_5$ are independently selected from aromatic, aliphatic, alkoxy, cyclic aliphatic, ether, halogen, hydrogen, and functional groups including selected from amine, amide, carboxyl, carboxylic acid, ester, nitro, nitroso, sulfate, sulfhydryl, phosphate, and $R_6$-$R_8$ are independently selected from aliphatic, and hydrogen, an acrylate derivative having a formula

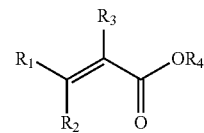

where $R_1$-$R_4$ are independently selected from aliphatic and hydrogen, or a combination thereof.

13. The valve according to claim 1, wherein the valve is operable to control fluid passage through a pore.

14. The photoactuatable valve according to claim 1, wherein the photoactuatable valve is associated with a photochromic flow path that is re-patternable by light exposure.

* * * * *